United States Patent [19]

Sprinzak

[11] 4,066,785
[45] Jan. 3, 1978

[54] ESTERS OF α-HYDROPEROXY-BIS-P-HALO-PHENYLACETIC ACIDS

[75] Inventor: Yair Sprinzak, Rehovoth, Israel

[73] Assignee: Yeda Research & Development Co., Ltd., Rehovot, Israel

[21] Appl. No.: 416,078

[22] Filed: Nov. 15, 1973

Related U.S. Application Data

[62] Division of Ser. No. 784,911, Dec. 18, 1968, Pat. No. 3,773,811.

[30] Foreign Application Priority Data

Dec. 26, 1967 Israel .......................................... 29228
Mar. 8, 1968 Israel .......................................... 29602

[51] Int. Cl.$^2$ ............................................. A01N 9/24

[52] U.S. Cl. ....................................................... 424/308
[58] Field of Search ........................... 424/308; 260/469

[56] References Cited

U.S. PATENT DOCUMENTS

3,279,983  10/1966  Baker et al. ...................... 424/219 X
3,471,572  10/1969  Hennessey ........................ 424/308 X Primary Examiner—Allen J. Robinson
Attorney, Agent, or Firm—Ostrolenk, Faber, Gerb & Soffen

[57] ABSTRACT

New esters of the α-hydroperoxy-bis-p-chloro-(or-bromo)-phenylacetic acids useful as acaricides, process for the preparation of same and compositions containing such materials.

3 Claims, No Drawings

ESTERS OF α-HYDROPEROXY-BIS-P-HALO-PHENYLACETIC ACIDS

This is a division of application Ser. No. 784,911, filed Dec. 18, 1968, and now U.S. Pat. No. 3,773,811.

FIELD OF THE INVENTION

The present invention relates to esters of the α-hydroperoxy-bis-p-chloro-(or-bromo)-phenylacetic acids.

SUMMARY OF THE INVENTION

The present invention relates to esters of the following formula:

$$(p\text{-}R'C_6H_4)_2C(OOH)\text{--}COOR \qquad (I)$$

in which R' is chloro or bromo and R may be an alkyl radical having from 1 to 5 carbon atoms and including both unsubstituted and substituted groups, e.g., methyl, ethyl, i-propyl, n-butyl, s-butyl, n-amyl; an allyl radical including both unsubstituted and substituted allyl groups; a cycloalkyl radical having from 5 to 7 carbon atoms in the nucleus thereof and including both unsubstituted and substituted groups, e.g. cyclohexyl; an aryl radical including both unsubstituted and substituted aryl groups; and an aralkyl radical having from 1 to 3 carbon atoms in the alkyl chain thereof and including both unsubstituted and substituted aralkyl groups, e.g. benzyl.

The esters of formula I are suitable agents for destroying vermin and, in particular, are excellent acaricides. Thus, for example, it has been found that various of such esters are very effective against rust mites, common red mites and citrus bud mites. The esters may be applied alone to the plants or the soil or they may be formulated on granules for application with a conventional fertilizer spreader, as an emulsifiable concentrate or a wettable powder for application as dilute sprays, as a dust for application with a conventional duster, or adsorbed on activated carbon for application on seeds.

The acaricidal compounds hereof are effective when employed in dilute concentrations. It is preferred, therefore, to incorporate the compounds in a variety of suitable solid or liquid carriers or diluents. Such compositions can be prepared either as a suspension in a suitable non-solvent or as a dust. A suspension or dispersion of the acaracidal compound in a non-solvent such as water may be prepared for direct application to infested plants or soil. Alternatively, a prepared suspension of the compound may be modified by the addition thereto of a commercially available dispersing or surface active agent. Examples of surface active compounds so useful are: An ethylene oxide condensate nonionic emulsifier; alkyl aryl sulfonates, e.g. calcium dodecyl benzene sulfonate.

In the preparation of dusts, the acaricidal compound may be admixed with a finely divided inert granular material as a carrier in any conventional manner. Useful carriers include kaolin, bentonite, talc, pumice, silica, chalk, wood flour, fuller's earth, activated carbon, charcoal and the like.

The esters of formula I are also useful as chemical intermediates for use in the preparation of the following formula $$(p\text{-}R'C_6H_4)_2C(OH)\text{--}COOR \qquad (II)$$

in which R and R' have the same meaning as set forth above. The esters of formula I can readily be converted into those of formula II, which are known pesticides (see, for example, R. Gasser, Experientia, Vol. VIII/2, p. 65 (1952)), by way of reduction reactions.

The present invention also comprises a process for the preparation of esters of formula I, which comprises oxidizing an ester of the following formula:

$$(p\text{-}R'C_6H_4)_2CHCOOR, \qquad (III)$$

in which R and R' have the same meaning as set forth above, with oxygen in an inert organic solvent and in the presence of a catalyst consisting essentially of a solid anhydrous alkali metal hydroxide and a small amount of alcohol.

PREFERRED EMBODIMENTS OF THE INVENTION

The preferred α-hydroperoxy-bis-p-halo-phenylacetic acid esters useful as acaricides in accordance with the present invention are ethyl and isopropyl α-hydroperoxy-bis-p-bromophenylacetate, ethyl and isopropyl α-hydroperoxy-bis-p-chlorophenylacetate. These materials have been found to possess particularly efficacy against a wide variety of mites, particularly rust mites, common red mites and citrus bud mites, as stated hereinabove.

The above novel esters and other esters of formula I are prepared from the corresponding esters of formula III. Such ester reactants are either known per se or may be prepared by esterification of the known acids. The reaction is, as previously noted, carried out in the presence of a catalyst consisting essentially of from about 0.25 to 0.75 parts by weight of an anhydrous alkali metal hydroxide, e.g. lithium, sodium or potassium hydroxide (the latter being preferred) to 1 part of the ester of formula III, and a suitable alcohol, e.g. a monohydric alkanol, such as methanol, ethanol, isopropanol, n-butanol or t-butanol in an amount corresponding to about 4 to 12% of the amount of the hydroxide.

The oxidation reaction is carried out in an inert organic solvent which should be inert to the initial ester reactant (of formula III), to the catalyst, and to the reaction product (of formula I). The inert solvent should also effect dissolution of at least a substantial proportion of the ester reactant. As suitable solvents there may be mentioned aliphatic hydrocarbons, e.g. n-heptane; aromatic hydrocarbons, e.g. toluene; chlorinated hydrocarbons, e.g. chlorobenzene; ethers, e.g. isopropyl ether, tetrahydrofuran and the like. In the event that the solvent comprises an alcohol in whole or in part, the further alcohol component of the catalyst composition may be partially or entirely eliminated.

The synthesis of the esters hereof is preferably performed at temperatures below room temperature, advantageously at or below 0°. (All temperatures are indicated herein as degrees centigrade).

The oxidation may be performed with any suitable oxidizing medium, e.g. with pure oxygen or with air.

The invention will be illustrated by the following specific examples but is is not intended that the invention be limited in any manner by them.

EXAMPLE 1

A mixture comprising 12.92 g of isopropyl bis-p-chlorophenylacetate, 180 ml of toluene, 8 g of powered anhydrous potassium hydroxide and 0.07 ml of ethanol was kept at 0° and stirred in an atmosphere of oxygen whereupon absorption of oxygen took place. Another 0.07 ml of ethanol was added when 120 ml of oxygen had been absorbed, the total volume of oxygen absorbed amounting finally to one liter, the mixture being stirred as long as the oxygen absorpttion took place.

The supernatant liquid was poured into a dilute solution of sodium hydrogen carbonate, the organic layer was separated and washed with water, the toluene was distilled off under reduced pressure to yield 13.17 g of crystalline isopropyl α-hydroperoxy-bis-p-chlorophenylacetate, m.p. 95°–97°. On recrystallization from petroleum/ether, the product melted at 100°–101°.

Analysis: C = 57.65% H = 4.50% Active oxygen: [O] = 4.5%.

This compound is very effective against common red mites, rust mites and against citrus bud mites.

Against the common red mite after 24 hours $LD_{50}$ was 0.009%.

The following experiment was performed to test the activity against rut mites:

Branches of Shamouti orange trees heavily populated with rust mites were sprayed with an emulsion of 0.03% isopropyl α-hydroperoxy-bis-p-chlorophenylacetate. Counts made 5 and 47 days after treatment revealed no mites on the treated branches, while infestation of the untreated branches remained high. No burns or spots were observed in either fruit or leaves.

EXAMPLE 2

The oxidation of isopropyl bis-p-chlorophenylacetate was carried out as described in Example 1, except that the ethanol was replaced by t-butyl alcohol.

6.46 g of the acetate yielded 6.80 g of the hydroperoxyacetate, m.p. 94°–96°. On recrystallization the product melted at 100°–101°.

EXAMPLE 3

A mixture of 6.46 g of isopropyl bis-p-chlorophenylacetate, 90 ml of isopropyl ether and 4 g of powdered, anhydrous potassium hydroxide was oxidized as described in Example 1. 0.2 ml of ethanol was added to the mixture after 260 ml of oxygen had been absorbed. The total volume of oxygen absorbed amounted to 500 ml.

The reaction mixture was worked up in the same manner as described in Example 1. The yield and the quality of the product were the same as those described in Example 1.

EXAMPLE 4

A solution of 6.46 g of isopropyl bis-p-chlorophenylacetate in 60 ml of tetrahydrofuran was added to a mixture of 30 ml of the same solvent and 4 g of powdered, anhydrous potassium hydroxide, kept at −18° and stirred in an atmosphere of oxygen. 470 ml of gas were absorbed.

The supernatant liquid was poured into a dilute solution of sodium hydrogen carbonate and the product extracted with benzene, the organic layer was washed with water, and evaporated to yield 6.22 g of isopropyl α-hydroperoxy-bis-p-chlorophenylacetate. It was washed with 10 ml of petroleum/ether to yield 5.34 g of the product, m.p. 96°–98°. After recrystallization from petroleum/ether, the product had a m.p. of 100°–101°.

EXAMPLE 5

An oxidation was carried out as described in Example 1, utilizing as starting material n-butyl bis-p-chlorophenylacetate and as solvent n-heptane, and performing the oxidation at −17°.

6.74 g of the ester yielded 7.00 g of n-butyl α-hydroperoxy-bis-p-chlorophenylacetate in the form of a thick oil. [O] = 3.9%.

EXAMPLE 6

An oxidation was carried out as described in Example 1, utilizing as starting material sec-butyl bis-p-chlorophenylacetate. 6.74 g of the latter yielded 7.10 g of crystalline sec-butyl α-hydroperoxy-bis-p-chlorophenylacetate, m.p. 92°–94°. On recrystallization from petroleum/ether, the product melted at 96°–97°.

Analysis: C = 52.87% H = 4.88% [O] = 4.3%.

EXAMPLE 7

An oxidation was carried out as described in Example 1, utilizing as starting material n-amyl bis-p-chlorophenylacetate, and performing the oxidation at −18°. 7.02 g of the latter yielded 7.50 g of n-amyl α-hydroperoxy-bis-p-chlorophenylacetate in the form of a thick oil.

Analysis: C = 59.53% H = 5.22% [O] = 3.9%.

EXAMPLE 8

A mixture comprising 5.90 g of methyl bis-p-chlorophenylacetate, 90 ml of chlorobenzene, 4 g of powdered anhydrous potassium hydroxide and 0.3 ml of ethyl alcohol was kept at −17° and stirred in an atmosphere of oxygen, whereby absorption of the gas took place. Stirring was continued to complete absorption, the total volume of oxygen absorbed amounting to 500 ml at atmospheric pressure and ambient temperature.

The reaction mixture was worked up as described in Example 1 to yield 6.25 g of methyl α-hydroperoxy-bis-p-chlorophenylacetate in the form of a thick oil. [O] = 4.3%.

EXAMPLE 9

A mixture of 6.18 g of ethyl bis-p-chlorophenylacetate, 90 ml of chlorobenzene and 4 g of powdered, anhydrous potassium hydroxide, kept at −18°, was stirred in an atmosphere of oxygen while small quantities of ethanol were being added thereto in order to maintain the absorption of the gas. 0.8 ml of ethanol were added, the volume of oxygen absorbed amounting to 500 ml.

The reaction mixture was worked up as described in Example 1, yielding 6.74 g of ethyl α-hydroperoxy-bis-p-chlorophenylacetate in the form of a thick oil. [O] = 4.3%.

This product is very effective against rust mites, common red mites and bud mites.

The following experiment was performed to test the activity against rust mites:

A tree of grape fruit heavily populated with rust mites was sprayed with an emulsion of 0.035% ethyl α-hydroperoxy-bis-p-chlorophenylacetate. Counts made after 6 and 51 days after treatment revealed no mites on the treated branches, while infestation of the untreated branches remained high.

EXAMPLE 10

An oxidation was carried out as described in Example 9, utilizing as starting material n-propyl bis-p-chlorophenylacetate and as solvent toluene. 6.46 g of the above ester yielded 7.10 g of n-propyl α-hydroperoxy-bis-p-chlorophenylacetate in the form of a thick oil. [O] = 4.0%.

EXAMPLE 11

A mixture comprising 7.68 g of methyl bis-p-bromophenylacetate, 90 ml of toluene, 4 g of powdered anhydrous potassium hydroxide and 0.3 ml of ethanol was kept at −18° and stirred in an atmosphere of oxygen whereupon absorption of oxygen took place. Stirring was continued to complete absorption, the total volume of oxygen absorbed amounting finally to 500 ml at ordinary pressure and temperature.

The supernatant liquid was poured into a dilute solution of sodium hydrogen carbonate, the organic layer was separated and washed with water, and the toluene was distilled off under pressure to yield 7.92 g of methyl α-hydroperoxy-bis-p-bromophenylacetate, m.p. 78°-83°. On recrystallization from petroleum/ether, the product melted at 83°-84°.

Analysis: C = 43.57% H = 2.89% Active oxygen: [O] = 3.7%.

EXAMPLE 12

An oxidation was carried out as described in Example 11, utilizing as starting material ethyl bis-p-bromophenylacetate, 7.96 g of the ester yielded 8.52 g of ethyl α-hydroperoxy-bis-p-bromophenylacetate in the form of a thick oil, which crystallized on treatment with petroleum/ether, m.p. 52°-54°. [O] = 3.7%.

EXAMPLE 13

An oxidation was carried out as in Example 11, utilizing as starting material isopropyl bis-p-bromophenylacetate, and performing the oxidation at 0°. 8.24 g of the ester yielded 8.74 g of isopropyl α-hydroperoxy-bis-p-bromophenylacetate, m.p. 85°-87°. On recrystallization from petroleum/ether the product melted at 88°-89°.

Analysis: C = 46.05% H = 3.57% [O] = 3.6% Against the common red mites after 24 hours the $LD_{50}$ was 0.0052%.

EXAMPLE 14

An oxidation of isopropyl bis-p-bromophenylacetate was carried out as in Example 11, utilizing as solvent chlorobenzene and performing the oxidation at 0°. 8.24 g of the ester yielded 8.75 g of isopropyl α-hydroperoxy-bis-bromophenylacetate, m.p. 83°-87°, which on recrystallization from petroleum/ether melted at 88°-89°.

EXAMPLE 15

An oxidation was carried out as in Example 11, utilizing as starting material isopropyl bis-p-bromophenylacetate and as solvent n-heptane, and performing the oxidation at 0°. Isopropyl α-hydroperoxy-bis-p-bromophenylacetate was obtained in the same yield and quality as in Example 14.

EXAMPLE 16

A solution of 8.24 g of isopropyl bis-p-bromophenylacetate in 60 ml of tetrahydrofuran was added to a mixture of 30 ml of tetrahydrofuran and 4 g of powdered anhydrous potassium hydroxide, kept at −18° and stirred in an atmosphere of oxygen. 460 ml of oxygen were absorbed.

The supernatant liquid was poured into a dilute solution of sodium hydrogen carbonate and the product extracted with benzene, the organic layer was washed with water and evaporated to yield 8.05 g of isopropyl α-hydroperoxy-bis-p-bromophenylacetate, m.p. 82°-87°, which on recrystallization from petroleum/ether melted at 88°-89°.

EXAMPLE 17

An oxidation was carried out as in Example 11, utilizing as starting material allyl bis-p-bromophenylacetate. 8.20 g of the ester yielded 8.80 g of allyl α-hydroperoxy-bis-p-bromophenylacetate in the form of a thick oil.

EXAMPLE 18

An oxidation was carried out as in Example 11, utilizing n-butyl bis-p-bromophenylacetate as starting material. 8.52 g of the ester yielded 8.90 g n-butyl α-hydroperoxy-bis-p-bromophenyl acetate, m.p. 60°-64°, which after washing with petroleum/ether melted at 64.5°-65.6°.

Analysis: C = 47.24% H = 3.81% [O] = 3.8%.

EXAMPLE 19

An oxidation was carried out as in Example 11, utilizing sec-butyl- bis-p-bromophenylacetate as starting material and isopropyl ether as solvent, and performing the oxidation at 0°. 8.52 g of the ester yielded 8.76 g of sec-butyl α-hydroperoxy-bis-p-bromophenylacetate, m.p. 92°-94°, which an recrystallization from petroleum/ether melted at 95°-95.7°. Analysis: C = 47.33% H = 3.95% [O] = 3.5%.

EXAMPLE 20

An oxidation was carried out as in Example 11, utilizing as starting material n-amyl bis-p-bromophenylacetate, 8.80 g of the ester yielded 9.08 g of n-amyl α-hydroperoxy-bis-p-bromophenylacetate, m.p. 56°-60°, which after washing with petroleum/ether, melted at 66.5°-67.5°.

EXAMPLE 21

An oxidation was carried out as in Example 1, utilizing as starting material cyclohexyl bis-p-chlorophenylacetate. 7.26 g of the ester yielded 7.5 g of cyclohexyl α-hydroperoxy-bis-p-chlorophenylacetate, m.p. 91°-93°. After recrystallization from petroleum/ether the product had a m.p. of 93.5°-94.5°. [O] = 4.0%.

EXAMPLE 22

An oxidation was carried out as in Example 1, utilizing as starting material benzyl bis-p-chlorophenylacetate and performing the oxidation at −18°. 7.42 g of the ester yielded 7.87 g of benzyl α-hydroperoxy-bis-p-chlorophenylacetate in the form of a thick oil. [O] = 3.7%.

What is claimed is:

1. A method of controlling acarid populations which comprises applying an acaricidally effective amount of an ester of the formula

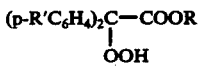

in which R is allyl and R' is bromine, to plants or soil in need of such control.

2. A method of controlling acarid populations which comprises applying an acaricidally effective amount of an ester of the formula

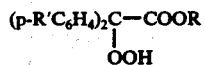

in which R is cyclohexl and R' is chlorine, to plants or soil in need of such control.

3. A method of controlling acarid populations which comprises applying an acaricidally effective amount of an ester of the formula

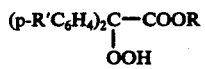

in which R is benzyl and R' is chlorine, to plants or soil in need of such control.

* * * * *